United States Patent [19]

Zaromb

[11] Patent Number: 5,106,756
[45] Date of Patent: * Apr. 21, 1992

[54] METHOD AND SYSTEM FOR GATHERING A LIBRARY OF RESPONSE PATTERNS FOR SENSOR ARRAYS

[75] Inventor: Solomon Zaromb, Hinsdale, Ill.

[73] Assignee: The United States of America as represented by the United States Department of Energy, Washington, D.C.

[*] Notice: The portion of the term of this patent subsequent to Dec. 19, 2006 has been disclaimed.

[21] Appl. No.: 452,014

[22] Filed: Dec. 18, 1989

Related U.S. Application Data

[63] Continuation-in-part of Ser. No. 881,310, Jul. 2, 1986, Pat. No. 4,888,295, which is a continuation-in-part of Ser. No. 585,699, Mar. 2, 1984, Pat. No. 4,670,405.

[51] Int. Cl.⁵ .................................................. G01N 33/02
[52] U.S. Cl. ........................... 436/161; 73/23.31; 73/23.36; 73/23.4; 73/23.41; 73/61.1 C; 364/498; 422/70; 422/89; 422/98; 436/151; 436/175; 436/177
[58] Field of Search ............... 73/23.1, 61.1 C, 23.31, 73/23.36, 23.4, 23.41; 422/70, 89, 98; 436/161, 175, 151, 177; 364/496, 497, 498

[56] References Cited

U.S. PATENT DOCUMENTS

| | | |
|---|---|---|
| 3,352,643 | 11/1967 | Ando et al. . |
| 3,653,840 | 4/1972 | Silas . |
| 3,706,381 | 12/1972 | Joynes et al. . |
| 3,902,848 | 9/1975 | Juvet, Jr. et al. . |
| 4,059,406 | 11/1977 | Fleet . |
| 4,181,853 | 1/1980 | Abu-Shumays et al. ....... 436/161 X |
| 4,383,433 | 5/1983 | Stacy ........................... 73/23.1 |
| 4,404,065 | 9/1983 | Matson . |
| 4,431,919 | 2/1984 | Kostlin et al. . |
| 4,440,726 | 4/1984 | Coulson . |
| 4,496,454 | 1/1985 | Berger . |
| 4,511,659 | 4/1985 | Matson . |
| 4,540,548 | 9/1985 | Imai et al. ................... 422/70 X |
| 4,542,640 | 9/1985 | Clifford ...................... 422/98 X |
| 4,549,965 | 10/1985 | Davis ........................ 436/161 X |
| 4,552,013 | 11/1985 | Matson . |
| 4,670,405 | 6/1987 | Stetter et al. . |
| 4,829,008 | 5/1989 | Zaromb . |

FOREIGN PATENT DOCUMENTS

| | | | |
|---|---|---|---|
| 57-135355 | 8/1982 | Japan ............................ 436/161 |
| 903765 | 2/1982 | U.S.S.R. ....................... 436/161 |

Primary Examiner—Robert J. Warden
Assistant Examiner—Timothy M. McMahon
Attorney, Agent, or Firm—Hugh W. Glenn; Robert J. Fisher; William R. Moser

[57] ABSTRACT

A method of gathering a library of response patterns for one or more sensor arrays used in the detection and identification of chemical components in a fluid includes the steps of feeding samples of fluid with time-spaced separation of known components to the sensor arrays arranged in parallel or series configurations. Modifying elements such as heating filaments of differing materials operated at differing temperatures are included in the configurations to duplicate operational modes designed into the portable detection systems with which the calibrated sensor arrays are to be used. The response patterns from the known components are collected into a library held in the memory of a microprocessor for comparison with the response patterns of unknown components.

19 Claims, 6 Drawing Sheets

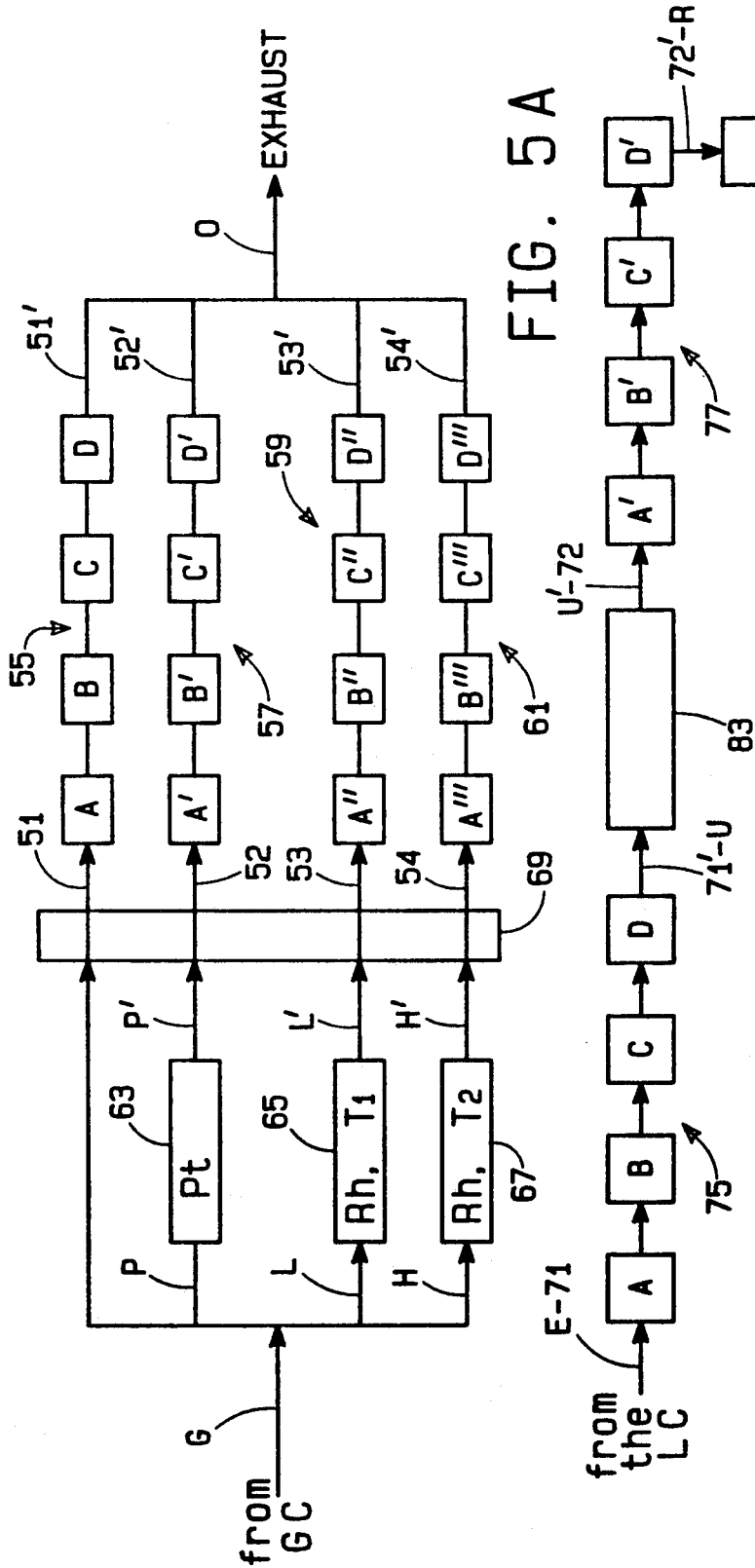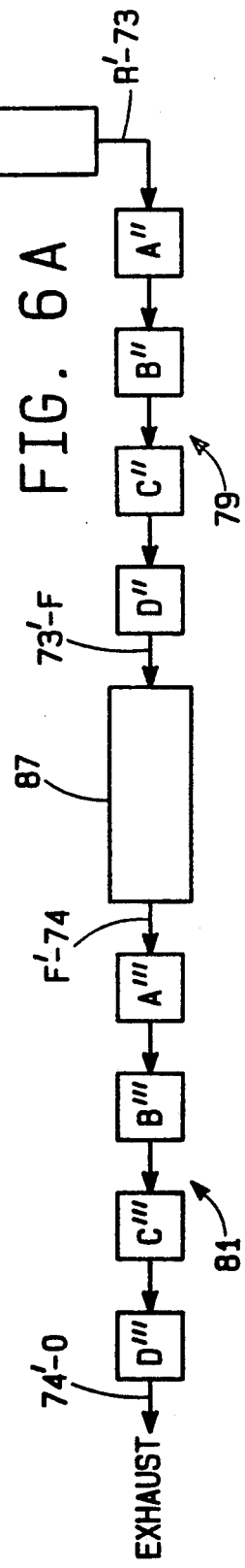
FIG. 5A
FIG. 6A

METHOD AND SYSTEM FOR GATHERING A LIBRARY OF RESPONSE PATTERNS FOR SENSOR ARRAYS

CONTRACTUAL ORIGIN OF THE INVENTION

The United States Government has rights in this invention pursuant to Contract No. W-31-109-ENG-38 between the U.S. Department of Energy and the University of Chicago representing Argonne National Laboratory.

CROSS-REFERENCE TO RELATED APPLICATIONS

This application is a continuation-in-part of U.S. application Ser. No. 881,310, filed July 2, 1986, by "Portable System and Method Combining Chromatography and Array of Electrochemical Sensors" which is a continuation-in-part of U.S. patent application Ser. No. 585,699, filed Mar. 2, 1984, now U.S. Pat. No. 4,670,405. These related applications are hereby incorporated by reference herein.

BACKGROUND OF THE INVENTION

The present invention relates to analytical instruments for detecting hazardous materials, and, in particular, to gathering and organizing response pattern libraries for use in conjunction with portable instruments.

This invention relates to analytical devices and, more particularly, to devices for detecting the presence of at least one pollutant or other hazardous component in a fluid sample. Such devices are needed, for example, in hazardous waste activities, such as site surveys to determine the presence of pollutants, location and identification of contamination, as well as certification of the absence of contamination (e.g. during transport and storage of wastes), monitoring of waste streams, and maintenance and operation of facilities. Hazardous wastes may include a large number of different materials. Detection devices are known for detecting and measuring one or a few selected pollutants, but they are not designed to identify unknown pollutants. When a gas for analysis may contain an unknown pollutant, it is usually necessary to obtain a sample of the gas and send it to a laboratory for a remote analysis, a costly and time-consuming operation.

In the aforementioned copending U.S. application Ser. No. 881,310, and in U.S. Pat. No. 4,670,405 there is disclosed a low-power, portable, analytical device for identifying hazardous components in a gas, such as air, through the use of an array of small sensors, such as electrochemical sensors, to provide a pattern of responses which is compared to a library of previously established response patterns to provide an identification of a component of the gas. The array also includes at least one heating filament capable of producing one or more derivatives by oxidation or pyrolysis of the component, so that the device is usable for detecting electrochemically inactive components. In addition, the responses from the sensors may be varied by changes in one or more of the operational conditions, such as voltage, temperature, sample flow rate, or diversion of the sample through a selective chemical filter and the like, so that the number of possible different responses is greater than the number of sensors and the number of detectable components in the gas. Analysis of the responses also provides data on the concentration levels of the hazardous component or components. That device has afforded adequate sensitivity for detecting hazardous components in concentrations as small as 1 ppm (parts per million).

U.S. patent application Ser. No. 881,310 also discloses a low-power, portable analytical device for use with the effluent from a liquid chromatographic column. Such a device has potential for detecting certain organic chemicals in trace amounts at low concentration without resorting to expensive, time-consuming methods. For example, primary aromatic amines in parts per billion concentrations will be detectable in the presence of much higher concentrations of interfering materials such as materials from coal tar.

In this sensitive analytical device, a small, compact liquid chromatographic system is combined with a chemical parameter spectrometer that includes one or more conditioning means in series with one or more arrays of electrochemical sensors. The conditioning means can include devices for ultraviolet irradiation, for injection of chemical luminescent or chemical reactive agents, filtering means or other implements for altering the characteristics of the sample.

In order to use a chemical parameter spectrometer (CPS) in combination with either a gas chromatographic (GC) or liquid chromatographic (LC) device, a library of known responses from the sensor arrays must be collected to permit the detection, identification and quantitative determinations of unknown components in a fluid flow. In previous procedures it was necessary to expose a sensor array several times to each compound that is to be included in the library. Where 20-30 or, in some instances, hundreds of chemical compounds or components are involved, several weeks of laboratory effort can be required to provide a response library for an individual sensor array.

The responses of electrochemical sensors as well as other sensors in their different modes of operation are known to change with time. The changes are neither the same nor parallel nor proportional for different compounds, so that it has not been possible heretofore to arrive at a satisfactory calibration procedure to correct for sensitivity changes that occur over time. Consequently, response pattern libraries can become obsolete and require substantial additional effort for recalibration.

SUMMARY OF THE INVENTION

Therefore, in view of the above, it is an object of the present invention to provide an improved method for gathering a library of response patterns for sensor arrays used in the detection of components of a fluid sample.

It is a further object to provide a rapid method for calibrating sensor arrays following a change in sensitivity over time.

It is yet another object to provide a method of calibrating a plurality of sensor arrays in a parallel or in a series flow arrangement.

It is likewise an object of the invention to provide a system for gathering and calibrating a library of response patterns for use in conjunction with a plurality of sensor arrays.

These and other objects of the invention are obtained by providing a method of gathering a library of response patterns for each of a plurality of sensor arrays to be used in the detection and identification of fluid-sample components. Each of the sensor arrays includes a plurality of sensors having differing electrical responses to at least one component or derivative thereof in the fluid sample. The method includes the steps of providing a plurality of samples with time-spaced separation of known components. One sample is provided for each sensor array to be calibrated. Each sensor is operated and the response pattern recorded for each of the operational modes contemplated for the portable detector.

In one manner of carrying out the method, a first sample is divided into a plurality of n parallel streams where n is the number of sensor arrays that are to be simultaneously calibrated. Each of the streams is selected to include a representative portion of each time-spaced component. The first of the parallel streams is passed through the first of the plurality of sensor arrays and the responses to each time-spaced component are recorded. The remaining parallel streams are simultaneously passed through separate conditioning devices to selectively alter the time-spaced components and then separately passed in parallel through the remaining sensor arrays. The responses to each time-spaced component are recorded to be a part of the response pattern library. Each of the remaining samples, in succession, is divided into a plurality of n parallel streams and processed in the manner described for the first sample but with suitable valving changes to subject each sensor array to the sample without conditioning and to the sample following conditioning by each of the conditioning devices. The recorded response to the time-spaced components are organized into respective libraries of response patterns corresponding to each of the sensor arrays for use in the detection and identification of fluid sample components.

In one embodiment of the invention, each sample of fluid is passed through a gas chromatographic or a supercritical fluid chromatographic column to provide time-spaced separations of components and selected parallel streams from each of the samples are conditioned by exposure to a heated platinum filament, a rhodium filament at a first temperature and a second rhodium filament at a second temperature higher than the first temperature.

In another embodiment, the time-spaced separation of known components is provided by a liquid chromatographic apparatus and all but the first of the parallel sample streams are separately conditioned by at least one of the conditioning steps including exposure to ultraviolet radiation, injection of a chemical luminescent agent, injection of a chemical reactive agent and filtering selective components from the sample.

An alternative method contemplates a series arrangement of sensor arrays and conditioning means through which n samples of fluid with time-spaced separation of known components are passed, where n equals the number of sensor arrays for which the libraries are to be prepared. In this method the sensor arrays are arranged in series flow with conditioning means positioned prior to all but the first of the sensor arrays. The conditioning means operates on one or more of the components in the fluid flow so as to selectively alter the responses thereto by the downstream sensor array. One of the samples of fluid is passed through the series arrangement and the response pattern to each time-spaced component is recorded. Subsequently the sensor arrays and conditioning means are rearranged into (n−1) differing arrangements with each of the sensor arrays in the first position in at least one arrangement. The remaining (n−1) samples are passed in sequence through the respective (n−1) arrangements and the response patterns recorded. The response patterns to the time-spaced components are recorded into libraries corresponding to each of the sensor arrays to be used in a series flow detection system.

In one other aspect of this method each of the conditioning means makes a different change in the time-spaced components from that made by the other conditioning means to provide differing responses from each of the downstream sensor arrays.

One other feature of the invention is a system for gathering a library of response patterns for each of a plurality of sensor arrays wherein each array includes a plurality of sensors having differing responses to at least one component or a derivative thereof which the sensors are designed to detect. The system includes a flow arrangement with a plurality of conditioning means for changing the characteristics of a fluid sample to provide a changed response from at least one sensor in an array receiving the sample. A plurality of positions are provided within the flow arrangement for receiving the sensor arrays to be investigated. An electrically programmable valving device is interconnected among the sensor arrays and the conditioning means to provide a plurality of configurations.

In more specific aspects of the system, a series configuration includes a first sensor array preceding an alternating sequence of conditioning means and sensor arrays. In addition, a parallel configuration is contemplated with a first sensor array in parallel with a plurality of conditioning means and sensor array couples arranged with the sensor array following the conditioning means. The programmable valving device is capable of rearranging the flow configuration so that each sensor array is preceeded by each of the conditioning means and so that each sensor array is accessible prior to any conditioning means. The system also includes recording means for receiving and recording response patterns corresponding to individual components in a time-spaced flow of components.

BRIEF DESCRIPTION OF THE DRAWINGS

The present invention is illustrated in the accompanying drawings wherein:

FIG. 5A is a schematic flow diagram showing one arrangement of the components achieved by the electrically programmable valve box of FIG. 5.

FIG. 6A is a schematic flow diagram showing a series flow arrangement of components achieved by the electrically programmable valve box of FIG. 6.

DESCRIPTION OF THE PREFERRED EMBODIMENTS

Figure 1:
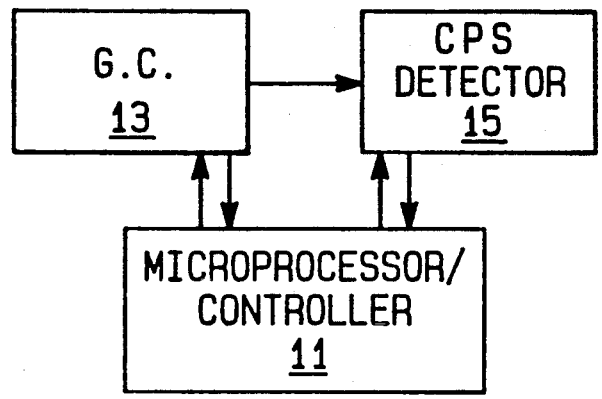
FIG. 1 is a block diagram of a portable system combining a gas chromatograph and a chemical parameter spectrometer.
Figure 2:
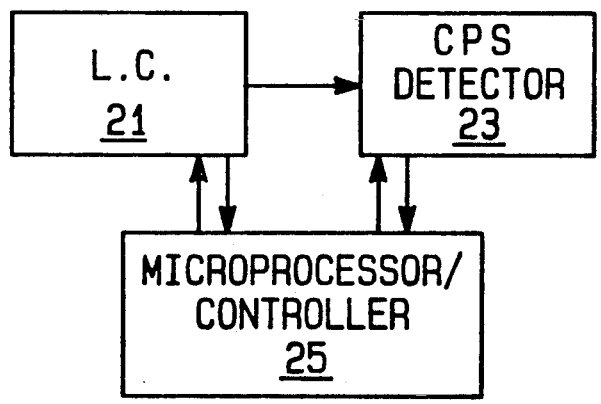
FIG. 2 is a block diagram with a system similar to FIG. 1 but combining a liquid chromatograph with a chemical parameter spectrometer.

FIGS. 1 and 2 respectively illustrate liquid and gas phase embodiments of portable systems combining chromatography with electrochemical and other sensors in a chemical parameter spectrometer (CPS). In FIG. 1 there is disclosed a gas system in which a microprocessor/controller 11 controls a gas chromatographic (GC) analyzer 13 and a CPS detector 15. In FIG. 2 there is illustrated a system including a liquid chromatographic analyzer 21, the eluent from which is fed through a CPS detector 23. Both the chromatographic analyzer 21 and the CPS detector 23 operate under the control of the microprocessor/controller 25.

Figure 3:
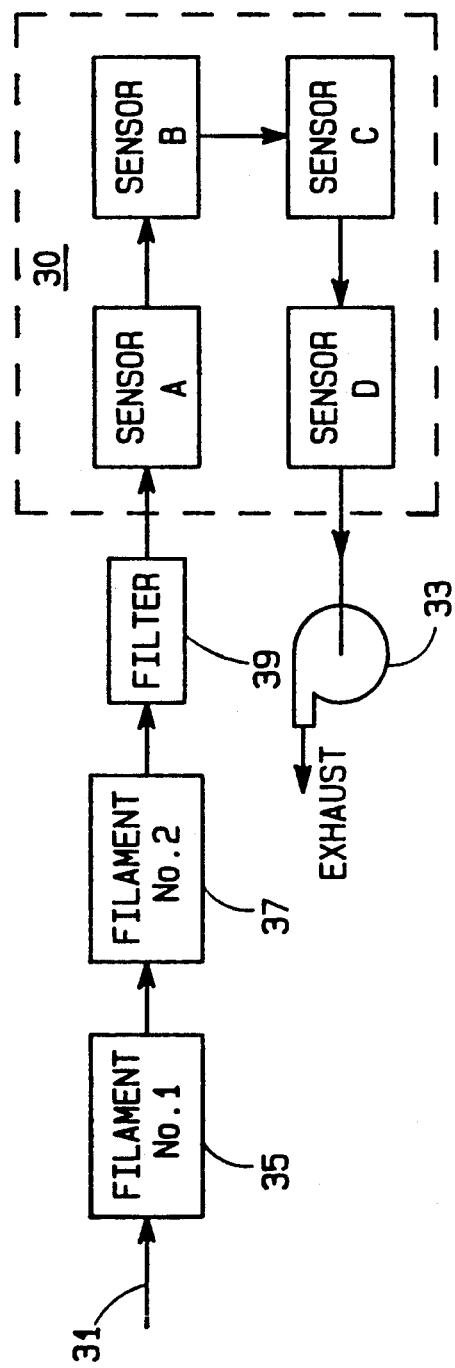
FIG. 3 is a block diagram of a chemical parameter spectrometer suitable for use in combination with a gas chromatograph.

In FIG. 3, one embodiment of the CPS detector is illustrated. A sample 31 from a GC column (not shown) or from ambient air flows to filaments 35 and 37 which may be individually switched on or off or both on and off during the analysis. Filter 39 is provided to remove particulates. The resulting sample may be the initial component or derivatives depending on whether filaments 35 and/or 37 are utilized. The resulting sample is then fed to sensor array 30 with sensors A, B, C and D arranged in sequence so that the first few sensors in the sequence interact with only minimum amounts of the sample without significantly altering the concentration introduced into sample chambers of the subsequent sensors. If ambient air is analyzed directly (without a GC column), then a pump 33 may be used to draw sample 31 through the series connected components. Sensor array 30 can be arranged in series as shown or in other configurations such as the parallel arrangement illustrated in FIG. 6 of the above-identified patent application Ser. No. 881,310. Other configurations of the sensor arrays in a CPS detector are illustrated in FIGS. 10 and 13 of the above cited application incorporated by reference herein for this purpose.

Figure 4:
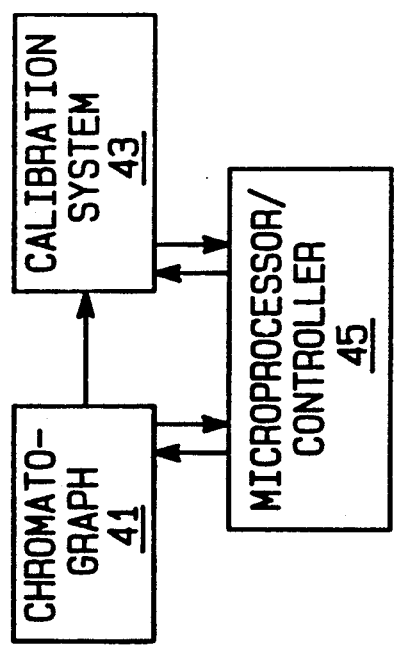
FIG. 4 is a block diagram of a calibration system suitable for use in gathering a library of response patterns.
Figure 5:
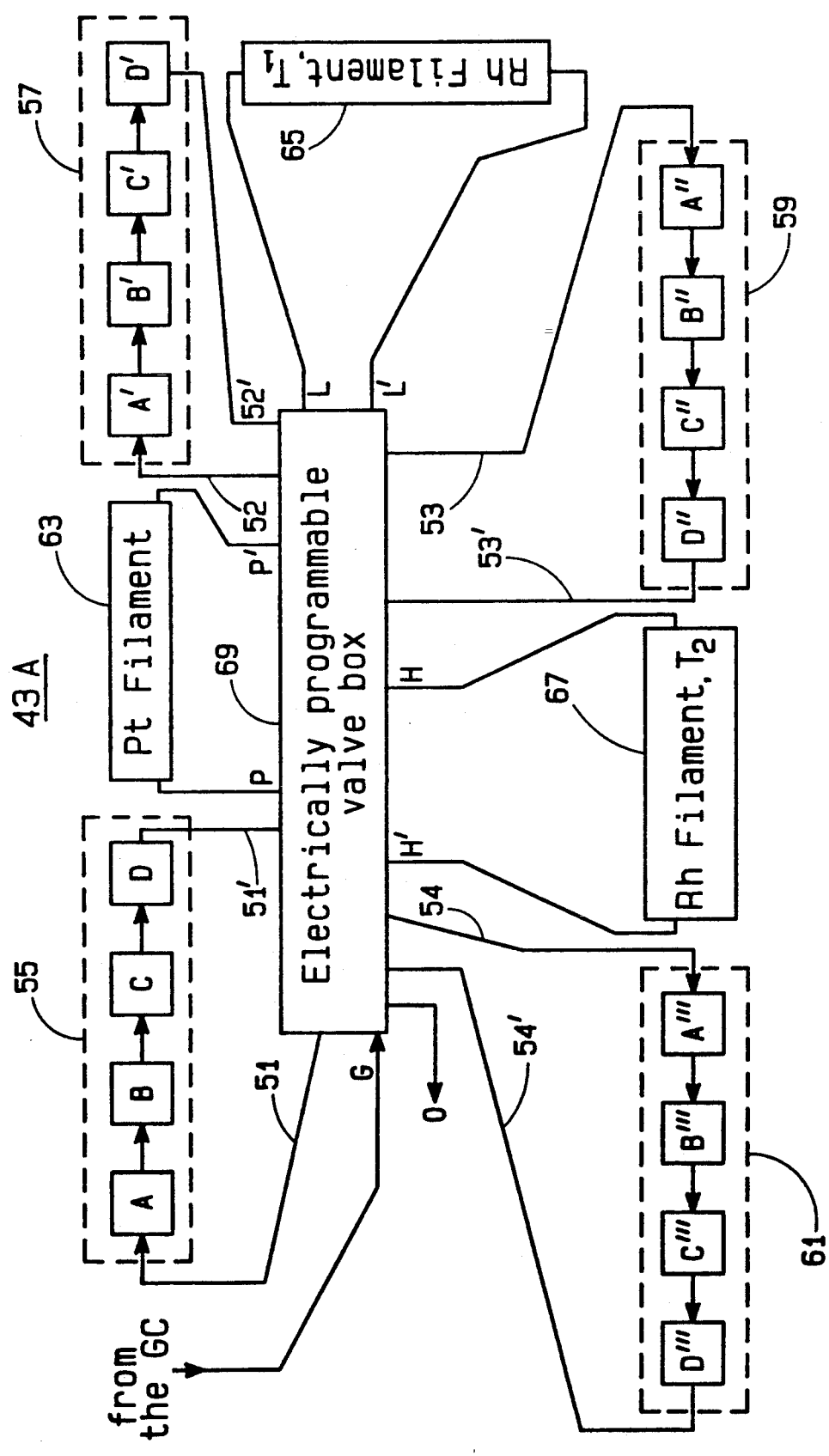
FIG. 5 is a block diagram of a calibration system that can be used with a gas chromatograph for calibrating and gathering libraries of response patterns for a plurality of sensor arrays.
Figure 6:
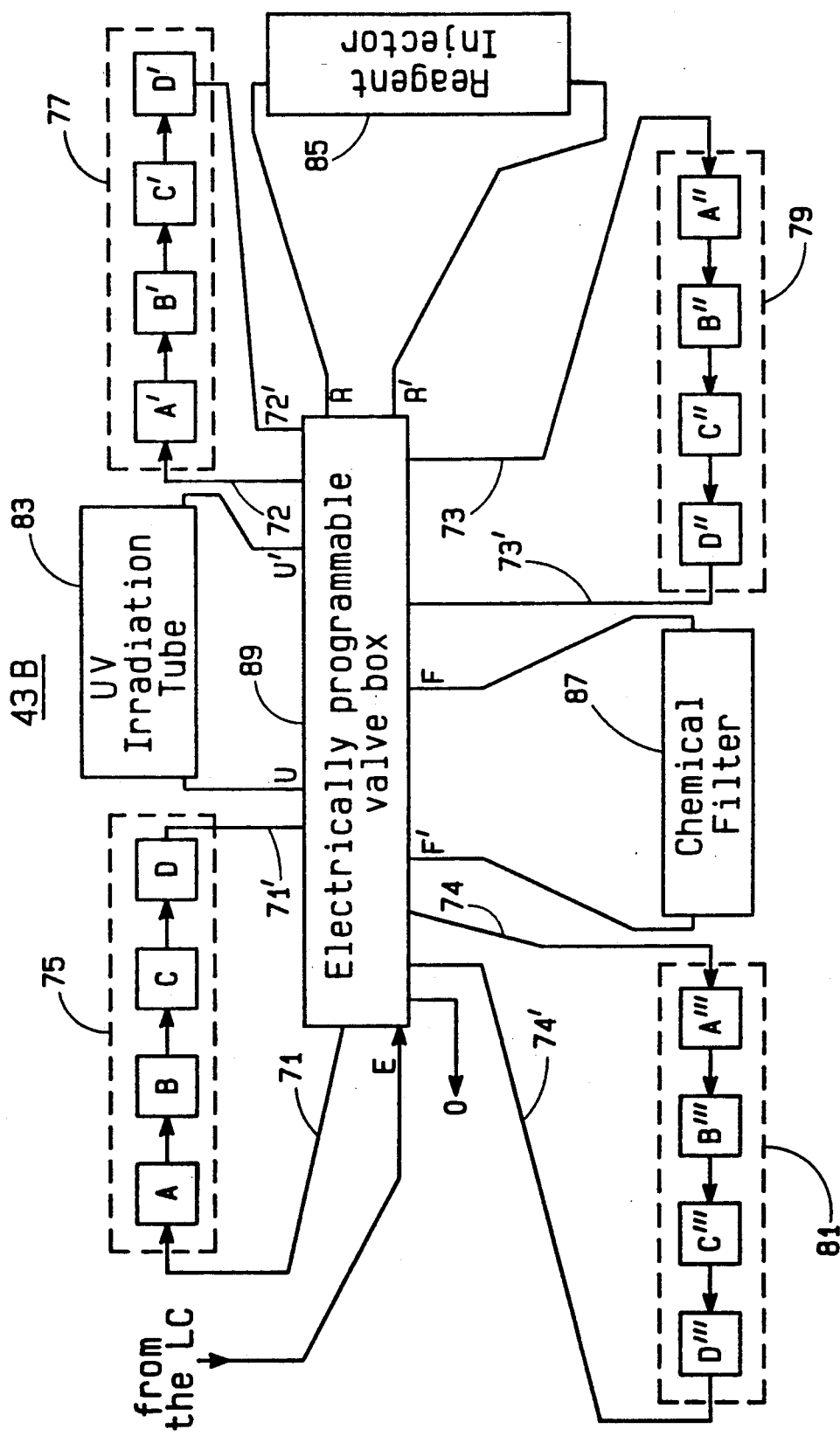
FIG. 6 is a block diagram of a calibration system similar to that shown in FIG. 5, but modified for use with a liquid chromatograph.

FIGS. 4, 5 and 6 illustrate systems for gathering libraries of response patterns for sensor arrays that will be used in chemical parameter spectrometers such as those described above and in the copending application incorporated by reference herein. A chromatograph 41 provides a sample of fluid with time-spaced separation of known components into a calibration system 43 including sensor arrays and other components of the chemical parameter spectrometer. The known components may derive, for instance, from a stable gas mixture of known composition that is injected into a gas chromatograph or from a stable liquid solution that is injected into either a gas chromatograph or a liquid chromatograph. The operation of the chromatograph and the calibration system is controlled and response data processed by the microprocessor/controller in a manner consistent with that of the microprocessor/controller employed with the portable detection system.

In FIG. 5, one embodiment of the calibration system 43 is illustrated in greater detail. A plurality of sensor arrays 55, 57, 59 and 61 are interconnected with filaments 63, 65 and 67 through an electrically programmable valve box 69 in various arrangements that will permit the calibration of each of the four sensor arrays.

Any one of these sensor arrays would be suitable for use as sensor array 30 illustrated in FIG. 3 where the filaments 35 and 37 correspond to the filaments 63, 65 and 67 illustrated in FIG. 5. For example, filament 37 could be a rhodium filament that is operated at first and second temperatures. These different operating modes will be accommodated in calibration system 43A by including two rhodium filaments 65 and 67 each operated at a different temperature.

In one embodiment of the calibration system 43, samples of known material with the time-space separation of several known components are provided from a packed GC column in line G to an electrically programmable valve box 69. In order to calibrate all four of the sensor arrays 55, 57, 59 and 61, four identical samples are provided in sequence. The number of samples provided will be equal to the number of sensor arrays to be calibrated in any calibration system arrangement.

In one manner of calibrating the sensor arrays, each sample is divided into n parallel streams with each stream containing a representative portion of each time-spaced component. In this system, n will equal the number of sensor arrays to be calibrated.

The first step in using a parallel flow arrangement is illustrated in FIG. 5A with the sample from the GC column divided into four parallel streams. The electrically programmable valve box 69 is arranged so that a first stream is passed through sensor array 55, a second sample stream is passed to platinum filament 63 and on to sensor array 57, a third sample stream is passed to rhodium filament 65 operated at a first temperature and then on to sensor array 59 and the fourth sample stream is passed to rhodium filament 67 operated at a second and higher temperature and then on to sensor array 61. Each sensor array discharge is connected to outlet 0 to exhaust the sample. The electrical output of the sensor arrays is transmitted to the microprocessor/controller 45, as is indicated in FIG. 4, for processing and recording each response in forming a library of response patterns.

The FIG. 5A arrangement comprises step 1 in the four-step procedure for processing each of the four identical samples from the GC column. Table 1 below gives the connections made by the electrically programmable valve box 69 for each of the four steps in a parallel flow arrangement. In this parallel arrangement many of the connections remain the same, requiring no action from programmable value box 69 through the four-step progression.

TABLE 1

| | Parallel Flow Connections | | |
|---|---|---|---|
| Step 1 | Step 2 | Step 3 | Step 4 |
| G-51 | G-52 | G-53 | G-54 |
| 51'-0 | 52'-0 | 53'-0 | 54'-0 |
| G-P | G-P | G-P | G-P |
| P'-52 | P'-51 | P'-54 | P'-53 |
| 52'-0 | 51'-0 | 54'-0 | 53'-0 |
| G-L | G-L | G-L | G-L |
| L'-53 | L'-54 | L'-51 | L'-52 |
| 53'-0 | 54'-0 | 51'-0 | 52'-0 |
| G-H | G-H | G-H | G-H |
| H'-54 | H'-53 | H'-52 | H'-51 |
| 54'-0 | 53'-0 | 52'-0 | 51'-0 |

As is seen from Table 1 the valve connections made in the four sequential steps permit each of the sensor arrays, 55, 57, 59 and 61, to be operated without modification of the sample and with the modifications provided by each of the filaments 63, 65 and 67.

FIG. 6 illustrates a calibration system 43B suitable for use with a liquid chromatographic (LC) column typically in a series flow operation. Four sensor arrays 75, 77, 79 and 81 are interconnected with an UV Irradiation Tube 83, a Reagent Injector 85 and a Chemical Filter 87 through a programmable valve box 89. Reagent injector 85 can be used to introduce chemical reactive and/or chemical luminescent agents for calibration of systems such as that illustrated and described in regard to FIG. 10 of application Ser. No. 881,310 incorporated by references herein. The valving connections for a series flow calibration are illustrated in Table 2 below with each of the four steps requiring the use of a separate but identical sample from the liquid chromatographic column.

TABLE 2

| | Series Flow Connections | | |
|---|---|---|---|
| Step 1 | Step 2 | Step 3 | Step 4 |
| E-71 | E-72 | E-73 | E-74 |
| 71'-U | 72'-U | 73'-U | 74'-U |
| U'-72 | U'-71 | U'-74 | U'-73 |
| 72'-R | 71'-R | 74'-R | 73'-R |
| R'-73 | R'-74 | R'-71 | R'-72 |
| 73'-F | 74'-F | 71'-F | 72'-F |
| F'-74 | F'-73 | F'-72 | F'-71 |
| 74'-O | 73'-O | 72'-O | 71'-O |

The first step in the calibration procedure for the series flow arrangement is illustrated for liquid samples in FIG. 6A with the four sensor arrays arranged in series with the UV-irradiated tube 83, the reagent injector 85 and the chemical filter 87. By changing the valving connections within the programmable valve box 89 according to Table 2, the arrangement can be modified in the remaining three steps so that each of the sensor arrays is alternately positioned in each of the four positions occupied by the sensor arrays 75, 77, 79 and 81 in the FIG. 6A arrangement.

The electrically programmable valve box can be any number of valving arrangements well known in the art. For example, electrically programmable solenoid valves, commercially available, can be readily designed for doing the parallel or series arrangements with suitable valving changes to permit each sensor array to receive and process the samples in each of the operating modes. For instance, the flow connections of Table 2 can be effected with a set of eight fur-way solenoid valves with each valve acting to effect the four steps required by a single line in Table 2.

Figure 6B:
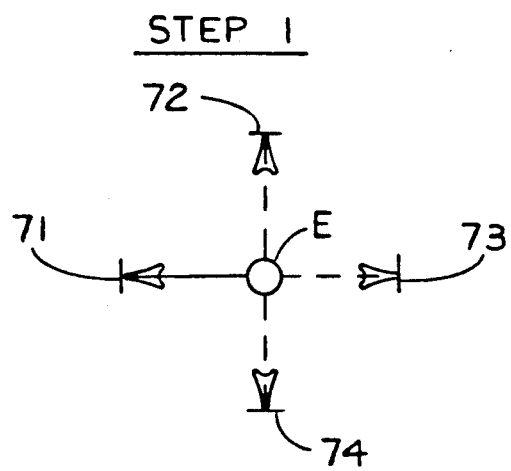
FIG. 6B, 6C, 6D and 6E are schematic illustrations of valves and valve settings suitable for use with the FIG. 6 calibration system.
Figure 6C:
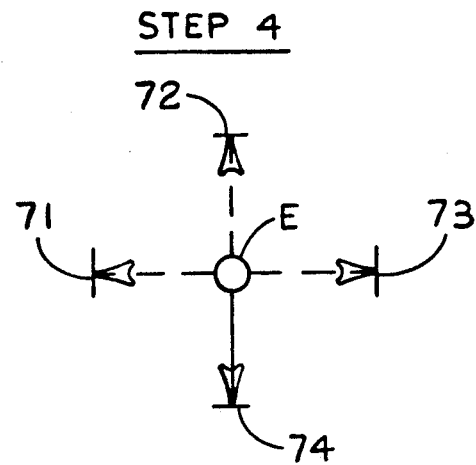
Figure 6D:
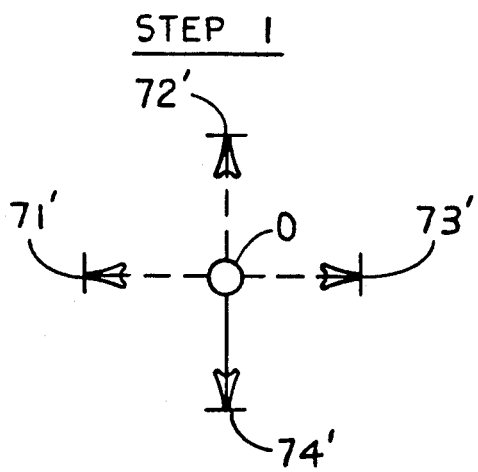
Figure 6E:
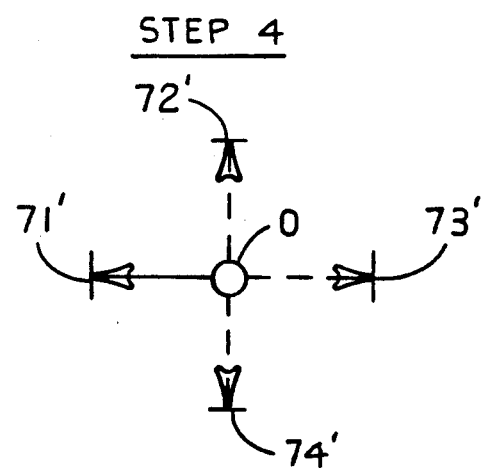

FIGS. 6B, 6C, 6D and 6E illustrate the valve settings for steps 1 and 4 in the first and last four-way valves corresponding to the first and last lines of Table 2. As illustrated, each of the four-way valves has a principal or center port and four peripheral ports. Operation of the valve permits selection of any one of the peripheral ports for connection to the center port. The solid arrows are the valve connections for these illustrated steps in Table 2 and the broken arrows are the alternative valve connections for the other required steps. For instance, the valve setting of FIG. 6B is seen to connect conduit E from the LC column to conduit 71 to sensor array 75. Similarly, other valve settings illustrated in FIGS. 6C, 6D and 6E, and those indicated by the remainder of Table 2 are made in the Electrically Programmable valve box 89 of FIG. 6 during the calibration of a series flow arrangement.

From the above it will be clear that a similar arrangement of four-way solenoid valves can be selected for use in the Electrically Programmable Valve Box 69 of FIG. 5. Since many of the connections given in Table 1 and illustrated in FIG. 5A remain unchanged during the four-step operation, valve box 69 can operate with as few as four of the four-way solenoid valves described above.

It will be appreciated that the individual sensor arrays can be calibrated to operate with the CPS detectors as described in conjunction with FIGS. 1-6 of the above-referenced U.S. Pat. No. 4,670,405 or U.S. patent application Ser. No. 881,310. Each of the CPS detectors produces a pattern of at least sixteen different sensor outputs which can then be compared in the microprocessor/controller 11 or 25 to a library of patterns accumulated with the present calibration device. The procedure can permit resolution of each chromatographic peak comparable to that achieved by some mass spectrometers. Using this procedure, the CPS detector works well for detecting, identifying and monitoring any one of about 20–30 compounds in air at concentrations in the ppm range.

From the foregoing, it can be seen that there has been provided an improved method for gathering a library of response patterns for the detection and identification of components in a fluid. The method permits rapid calibration of sensor arrays for use in portable detection devices.

Although the present invention is described in terms of specific materials and process steps, it will be clear to one skilled in the art that various changes and modifications may be made in accord with the invention as defined in the accompanying claims.

The embodiment of the invention in which an exclusive property or privilege is claimed is defined as follows:

1. A method of gathering a library of response patterns for one or more sensor arrays for use in the detection and identification of the chemical components of a fluid, each of the sensor arrays including a plurality of sensors having differing electrical responses to at least one component or derivative thereof, said method comprising:
   providing a sample of fluid with time-spaced separation of several known components;
   dividing the sample into a plurality of n parallel streams, each stream including a representative portion of each time-spaced component;
   passing the first of the parallel streams through the first of a plurality of sensor arrays and recording the sensor responses to each time-spaced component;
   simultaneous conditioning of the second through the n-th parallel stream to selectively alter the time-spaced components therein and then separately passing each of the second through n-th stream in parallel through a second to n-th sensor array respectively and recording the response to each time-spaced component;
   providing, in succession, second through n-th samples of fluid with time-spaced separation of known components;
   dividing each of the second through n-th samples into a plurality of n parallel streams, each stream including a representative portion of each time-spaced component;

passing one of the parallel streams from each of the second through n-th samples in succession, through the respective one of the second to the n-th sensor arrays and recording the sensor responses to each time-spaced component;

simultaneously conditioning each of the remaining parallel streams from each of the second through n-th samples to selectively alter the time-spaced components therein and then separately passing each of the remaining streams through one of the remaining n−1 sensor arrays and recording the sensor responses to each time-spaced component; and organizing the responses to the time-spaced components into respective libraries of response patterns corresponding to each of the sensor arrays for use in the detection and identification of said chemical components.

2. The method of claim 1 wherein the sample of fluid is passed through a gas chromatographic or supercritical fluid chromatographic column for achieving the time-spaced separations of components.

3. The method of claim 1 wherein the parallel sample streams are gaseous mixtures and each mixture is separately conditioned by contact with a heated filament to selectively alter the responses thereto of the corresponding sensor array.

4. The method of claim 3 wherein the heated filaments include a platinum filament, a rhodium filament at a first temperature and a second rhodium filament at a second temperature higher than the first temperature.

5. The method of claim 1 wherein the time-spaced separation of known components is provided by a liquid chromatographic apparatus.

6. The method of claim 5 wherein parallel sample streams are each separately conditioned by at least one of the conditioning steps including exposure to ultraviolet radiation, injection of a chemical luminescent agent, injection of a chemical reactive agent and/or filter for removing selected components from the sample.

7. A method of gathering a library of response patterns for one or more sensor arrays for use in the detection and identification of the chemical components of a fluid, each of the sensor arrays including a plurality of sensors having differing electrical responses to at least one component or derivative thereof, said method comprising:

providing n samples of fluid with time-spaced separation of known components, where n equals the number of sensor arrays for which the libraries are to be prepared;

arranging the sensor arrays in series flow with conditioning means positioned prior to all but the first of the sensor arrays in the series flow, the conditioning means operating on one or more of the components in the fluid so as to selectively alter the response thereto by the downstream sensor array;

passing one of the samples of fluid through the series arrangement of sensor arrays and recording the response pattern to each time-spaced component produced by each of the sensor arrays;

sequentially rearranging the series flow into n−1 differing arrangements with each of the sensor arrays in the first position in at least one arrangement; and passing the remaining n−1 samples in sequence through the respective n−1 arrangements and recording the response pattern to each time-spaced component.

organizing the responses to the time-spaced components into respective libraries of response patterns corresponding to each of the sensor arrays for use in the detection and identification of said chemical components.

8. The method of claim 7 wherein each of the conditioning means makes a different change in the time-spaced components from that made by the other conditioning means to provide differing responses from each of the downstream sensor arrays.

9. The method of claim 7 wherein a plurality of n liquid samples are passed through a liquid chromatographic device to provide time-spaced separation of components and the samples are conditioned prior to all but the first sensor array by at least one conditioning step selected from: exposing the sample to ultraviolet radiation; injecting chemical luminescent agents into the sample; injecting chemically reactive agents into the sample; and/or filtering selected components from the sample.

10. The method of claim 7 wherein said samples of fluid are obtained from a stable gas mixture of known composition.

11. The method of claim 7, wherein said samples of fluid are obtained form a stable liquid solution of known composition.

12. A system for gathering a library of response patterns for one or more sensor arrays, wherein each array includes one or more sensors having differing responses to at least one chemical component or a derivative thereof which the sensors are designed to detect, comprising:

a flow arrangement including one or more conditioning means for changing the characteristics of a fluid sample to provide a changed response from at least one sensor in an array receiving the sample;

a plurality of positions within the flow arrangement for receiving the sensor arrays;

valving means for interconnecting the sensor array or arrays with the conditioning means in a plurality of configurations, said valving means capable of rearranging the flow configuration so that each sensor array is preceded by each of the conditioning means and so that each sensor array is accessible prior to any conditioning means; and recording means for receiving and recording response patterns corresponding to individual components in a time-spaced flow of components.

13. The system of claim 12 wherein said flow arrangement can simultaneously calibrate two or more sensor arrays.

14. The system of claim 13 including a series configuration with a first sensor array preceding an alternating sequence of conditioning means and sensor arrays.

15. The system of claim 13, including a parallel configuration with a first sensor array in parallel with a plurality of conditioning means and sensor array couples arranged with the sensor array following the conditioning means.

16. The system of claim 12, wherein said valving means is electrically actuated.

17. The system of claim 12, including programming means for rearranging said flow configurations by said valving means.

18. The system of claim 12 comprising a gas chromatographic, liquid chromatographic or supercritical fluid chromatographic column, for achieving said time-spaced flow.

19. The system of claim 18, wherein said chromatographic column is a packed column.

* * * * *